United States Patent [19]

Saadat

[11] Patent Number: 5,658,275
[45] Date of Patent: Aug. 19, 1997

[54] SURGICAL LASER INSTRUMENT

[75] Inventor: Vahid Saadat, Irvine, Calif.

[73] Assignee: Trimedyne, Inc., Irvine, Calif.

[21] Appl. No.: 473,752

[22] Filed: Jun. 7, 1995

[51] Int. Cl.⁶ .................................................. A61B 17/36
[52] U.S. Cl. .................................................. 606/15; 606/17
[58] Field of Search ......................... 606/10, 11, 12, 606/14, 15, 16, 17, 4

[56] References Cited

U.S. PATENT DOCUMENTS

| | | | |
|---|---|---|---|
| 4,456,330 | 6/1984 | Bludaii | 350/96.18 |
| 4,592,353 | 6/1986 | Daikuzono | 606/15 |
| 4,693,244 | 9/1987 | Daikuzono | 606/15 |
| 4,736,743 | 4/1988 | Daikuzono | 128/4 |
| 4,832,024 | 5/1989 | Boussignac et al. | 606/15 |
| 5,071,222 | 12/1991 | Laakmann et al. | 385/125 |
| 5,151,098 | 9/1992 | Loertscher | 606/16 |
| 5,209,748 | 5/1993 | Daikuzono | 606/16 |
| 5,219,346 | 6/1993 | Wagnieres et al. | 606/16 |
| 5,290,280 | 3/1994 | Daikuzono | 606/17 |
| 5,292,320 | 3/1994 | Brown et al. | 606/17 |
| 5,303,324 | 4/1994 | Lundahl | 606/17 |
| 5,342,358 | 8/1994 | Daikuzono | 606/16 |
| 5,415,655 | 5/1995 | Fuller et al. | 606/17 |
| 5,456,681 | 10/1995 | Hajjar | 606/16 |
| 5,496,307 | 3/1996 | Diakuzono | 606/17 |

FOREIGN PATENT DOCUMENTS

WO 9321840  11/1993  WIPO.

OTHER PUBLICATIONS

Doty, et al. "The Laser Photocoagulating Dielectric Waiveguide Scalpel" *IEEE Transactions on Biomedical Engineering* BME–28, No. 1, 1–9 (Jan. 1981).

Primary Examiner—Lee S. Cohen
Assistant Examiner—Sonya Harris-Ogugua
Attorney, Agent, or Firm—Olson & Hierl, Ltd.

[57] ABSTRACT

A surgical laser instrument including a transparent, splay, plate-like waveguide including one or more discontinuities therewithin for flattening and expanding a laser beam received through the waveguide and for emitting therefrom a relatively flat laser beam that can be utilized to sweep a selected tissue or region to be treated.

41 Claims, 3 Drawing Sheets

SURGICAL LASER INSTRUMENT

FIELD OF THE INVENTION

The present invention relates to a surgical laser instrument suitable for the delivery of laser energy to a selected tissue region. More particularly, the present invention pertains to a surgical laser instrument suitable for delivering a flattened and expanded beam of laser energy to a selected tissue region.

BACKGROUND OF THE INVENTION

Laser energy has been used for treatment in medicine and surgery for many years. In order to deliver laser energy to the tissue to be treated, various types of laser beam delivery systems have been developed including systems incorporating laser energy waveguides at the distal ends thereof.

With these laser beam delivery systems, different tissue treating effects have been achieved by using differently sized and shaped waveguides to produce varied laser energy output distributions.

The most common such delivery systems include either a waveguide including a cone or pointed tip for delivering a concentrated, high energy beam of laser energy to a defined and concentrated tissue site or, alternatively, a circularly, spherically or cylindrically curved waveguide for delivering laser energy in a circular, spherical or cylindrical pattern to a region of selected tissue.

A disadvantage of the instrument including a pointed waveguide is that, although suitable for directing a concentrated high energy beam of laser energy to a defined tissue site to effect, for example, a cut, such instrument is not suitable for the efficient and cost effective treatment of a relatively larger tissue region.

Another disadvantage of emitting laser energy from the distal pointed or coned tip of an optical waveguide is the small "spot" size on tissue and the rapid divergence of the laser beam as the waveguide is moved away from the tissue.

The instrument including a circularly, spherically or cylindrically curved waveguide, although able to deliver energy to a region of tissue, is disadvantageous because it does so in a random or uneven pattern which results in some tissue being overexposed to the incident energy and some being underexposed. Round "spot" emissions make it difficult to produce an even exposure without the overlapping of energy exposures.

Thus, there continues to be a need for a surgical laser instrument which allows for a controlled and cost effective treatment of a rectangular tissue region, e.g., for dermatology, tonsillectomy, and the like treatments and, more particularly, for a surgical laser instrument which allows a surgeon to evenly sweep or "paint" a large tissue area at a desired energy level.

SUMMARY OF THE INVENTION

A surgical instrument embodying the present invention permits a surgeon to evenly heat, coagulate and/or ablate relatively large tissue regions with a readily manipulatable laser energy beam.

The contemplated surgical instrument includes a hollow housing, a fiber optic mounted in the housing, and a solid, transparent waveguide that flattens a laser beam incident thereon from the distal end of the fiber optic mounted to the housing. The incident laser beam is flattened to a degree such that the laser beam emitted from the surgical instrument is at least three times wider than its thickness. The transparent waveguide has a refractive index that is higher than the refractive index of the fiber optic.

The preferred waveguide has a transparent, splay, i.e., flat and wide, body portion. This plate-like body portion includes therewithin a laser beam expander means which receives the laser beam emitted from the distal end of the fiber optic and transforms the emitted beam into a relatively flat laser beam that can be utilized to sweep a selected tissue site or region in a manner similar to a paint brush while performing a medical procedure that heats, coagulates and/or ablates tissue. The extent of tissue effect, whether by heating to cause cross-linking of collagen, coagulation, ablation, or a combined effect, depends upon the energy density of the transformed, relatively flat laser beam, the duration of tissue exposure thereto, as well as the laser wavelength.

According to the present invention, the beam expander means comprises at least one discontinuity defined in a transparent, splay body portion. In one embodiment of the present invention, the discontinuity is contained in the body portion and defines a region having an index of refraction that is less than the index of refraction of the body portion. In an alternate embodiment, the beam expander means may comprise additional contained discontinuities positioned on opposite sides of the first discontinuity generally centrally between incident and emitting faces of the transparent body portion and adjacent the peripheral side faces of the body portion. Such contained discontinuity or discontinuities may be a convertor lens such as a void defined in the body portion or, alternatively, an optical lens in the body portion.

The beam expander means may also comprise a surface discontinuity defined in the incident face of the body portion which, either individually or in combination with the contained discontinuities in the body portion, receive the laser beam emitted from the distal end of the fiber optic and transform the emitted beam into a relatively flat and expanded beam. In one preferred embodiment, the incident face surface discontinuity is defined by at least three contiguous arcuate surfaces having the configuration of grooves in the incident face which grooves extend into the body portion and are positioned generally centrally thereon to receive and expand the beam emitted from the fiber optic. In another embodiment, the incident face surface discontinuity is wedge-shaped and includes first and second flat surfaces which converge into the body portion toward the emitting face.

According to the present invention, the body portion of the waveguide may have any one of several configurations including a quadrate or sphenoid, e.g., cuneate, spatulate, or the like configuration.

The waveguide is mounted in a generally flat tip member at the end of the hollow housing. The tip member which includes a base, spaced apart arms extending outwardly from the base, and top and bottom support plates which are secured to the arms.

According to the present invention, the housing includes one or more apertures located adjacent the tip member. The apertures extend between the hollow interior and outer surface of the housing and define a passageway for water or a saline solution which is introduced into the hollow interior of the housing via a conduit connected to the end of the housing. The water or saline solution is used to cool the tissue as it is being treated to avoid thermal damage to the tissue.

Numerous other advantages and features of the present invention will become readily apparent from the following detailed description of the invention and the embodiments thereof, from the claims and from the accompanying drawings in which details of the invention are fully and completely disclosed as part of this specification.

DETAILED DESCRIPTION OF THE PREFERRED EMBODIMENTS

Figure 1:
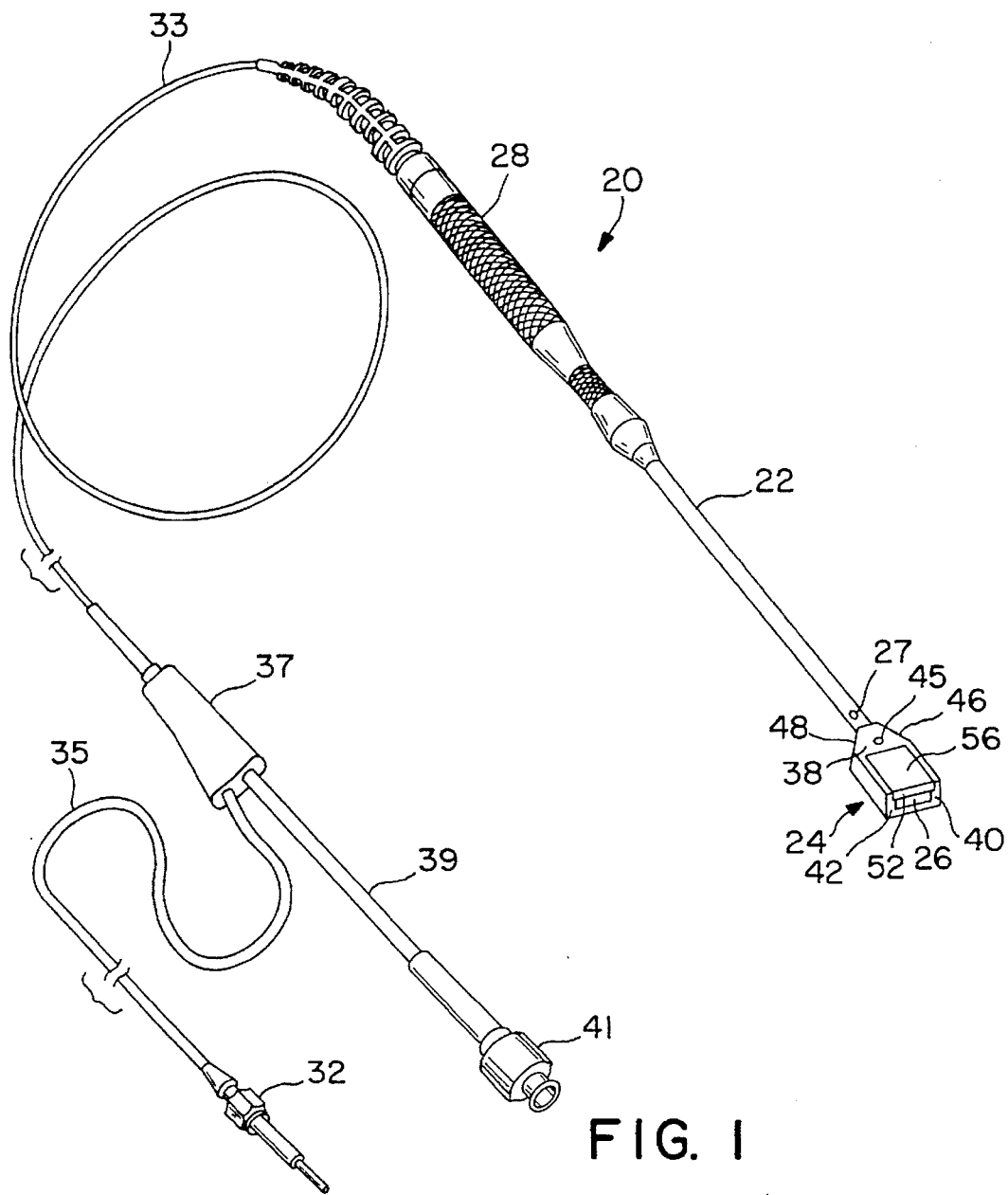
FIG. 1 is a perspective view of a surgical laser instrument embodying the features of the present invention.

While this invention is susceptible of embodiment in many different forms, there are shown in the drawings and will be described herein in detail specific embodiments thereof with the understanding that the present disclosure is to be considered as an exemplification of the principles of the invention and is not to be limited to the specific embodiments illustrated.

As shown in FIG. 1, one preferred embodiment of a surgical laser instrument 20 according to the present invention for directing laser energy to a selected tissue site or region comprises a hollow cylindrical housing or stem 22 that terminates into a generally flat tip member 24 defining an enclosure 25 (FIG. 2) for a solid, planar laser beam waveguide 26. The stem 22 and tip 24 are preferably made of stainless steel. However, other materials of metallic construction may be utilized as well.

Figure 2:
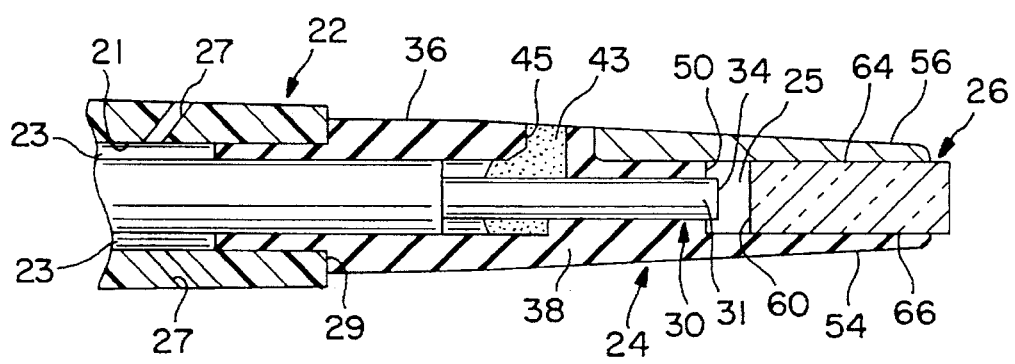
FIG. 2 is an enlarged side elevational view of the tip of the surgical laser instrument shown partly in section.

Referring to FIG. 2, the stem 22 includes an interior cylindrical surface 21 defining an interior cylindrical hollow passage 23. Stem 22 further includes a pair of opposed apertures 27 located adjacent the distal end 29 thereof. Apertures 27 extend at an angle between the interior cylindrical surface 21 and the outer cylindrical surface of stem 22.

Referring to FIGS. 1 and 2, a handpiece 28, made of plastic or the like, surrounds a portion of the stem 22. A fiber optic 30, with a core 31 preferably having a diameter of about 0.6 millimeters, extends through the interior passage 23 of stem 22 extending through handpiece 28, through the interior of a conduit 33 which is connected to the end of the stem 22 at the end of handpiece 28 and then through a conduit 35 connected to conduit 33 via splice 37. Fiber optic 30 includes a proximal end which is connected to a connector 32 at the end of conduit 35 for coupling the fiber optic 30 to a laser energy source (not shown) and a distal end 34 (FIG. 2) extending into the interior passage 23 of stem 22 and into the tip 24.

Referring to FIG. 1, instrument 20 further includes a conduit 39 having a distal end connected to conduit 33 via conduit splice 37 and a proximal end having a luer hub 41 connected thereto.

Tip member 24 is a generally flat member and includes a hollow stem portion 36 which is fitted to and secured within the proximal end 29 and, more particularly, the interior 23 of stem 22, a base portion 38 extending outwardly from and unitary with the stem portion 36, and a pair of spaced apart arms 40 and 42 extending outwardly from and unitary with base portion 38. Base portion 38 is defined by diverging peripheral side surfaces 46 and 48 and an end surface 50. Base portion 38 includes an aperture 45 which serves as a conduit for a potting compound 43 such as a room temperature vulcanizable silicone resin, which is used to secure the fiber optic 30 in the tip 24. The arms 40 and 42 extend outwardly from the surfaces 46 and 48, respectively. A shoulder 52 (FIG. 1) is defined around the periphery by the surface 50 and the arms 40 and 42.

The tip 24 further includes a bottom plate 54, unitary with and extending outwardly from the end surface 50 and between arms 40 and 42. Bottom plate 54 provides a bottom support surface for the waveguide 26. A top plate 56 is seated in and abuts the shoulder 52. The arms 40 and 42 in combination with the surface 50 and plates 54 and 56 define the enclosure 25 for waveguide 26.

Figure 3:
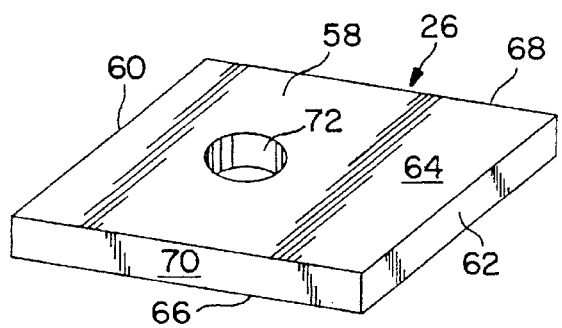
FIG. 3 is a perspective view of a quadrate waveguide according to the present invention.

As shown in FIG. 3, waveguide 26, which is shown therein in the configuration of a quadrate, includes a solid, transparent, plate-like or splay, i.e., flat and wide, body portion 58 including a laser energy incident face 60, a laser energy emitting face 62, and peripheral laser energy reflecting faces or surfaces therebetween, i.e., top and bottom faces or surfaces 64 and 66 and side faces or surfaces 68 and 70 surrounding body portion 58. Preferably, the waveguide 26 is 1 mm thick, about 3–5 mm long, and about 1.5 to 6 mm wide.

Waveguide 26 is secured in the enclosure 25 defined by tip member 24. The top and bottom peripheral faces 64 and 66 abut the top and bottom plates 56 and 54, respectively, and peripheral side faces 68 and 70 abut the arms 40 and 42, respectively, substantially along the entire length thereof. Moreover, incident face 60 of waveguide 26 is spaced from the distal end 34 of fiber optic 30 and is situated therein to receive a beam of laser energy emitted from the distal end 34 of fiber optic 30. Emitting face 62 protrudes or extends beyond the ends of arms 40 and 42. If desired, waveguide 26 may also be secured in tip 24 such that incident face 60 abuts the distal end 34 of fiber optic 30 or, alternatively, such that emitting face 62 is flush with the end of arms 40 and 42.

According to the present invention, the waveguide 26 is manufactured from a transparent laser energy transmitting material such as, but not limited to, fused silica, sapphire, diamond, zinc selenide, quartz and a host of other optically transparent materials having a refractive index higher than the refractive index of fiber optic 30. The peripheral faces 64, 66, 68 and 70 can be coated with a reflective material such as gold or the like or with fluoride doped glass or the like material having an index of refraction that allows for internal reflection of laser beam energy.

Figure 4:
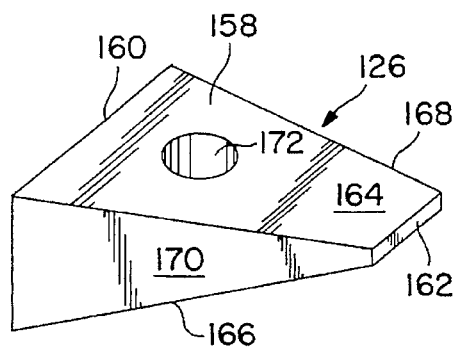
FIG. 4 is a perspective view of a sphenoid, e.g., cuneate, waveguide according to the present invention.

FIG. 4 depicts an illustrative waveguide 126 in the form of a sphenoid, e.g., cuneate or wedge configuration, including a body portion 158 having a laser energy incident face 160, a laser energy emitting face 162, peripheral faces 164–170 therebetween which converge inwardly toward emitting face 162, and a contained discontinuity 172.

Referring to FIG. 3, body portion 58 of waveguide 26 includes therewithin, and unitary therewith, laser beam expander means in the form of a circularly shaped, internally contained discontinuity 72 which provides a region having an index of refraction different than the index of refraction of the body portion 58 and, preferably, an index of refraction which is less than the index of refraction of body portion 58. This expedient expands the laser beam passing through incident face 60 into the body portion 58. The contained discontinuity 72 is positioned symmetrically about an axis substantially normal to the laser beam emitted from the fiber optic 30, i.e., positioned generally centrally between the peripheral side faces 68 and 70 and adjacent incident face 60.

Beam expanding discontinuities can take any one of several configurations including, but not limited to, the configurations shown in FIGS. 5 through 11 depending upon the desired performance requirements.

Figure 5:
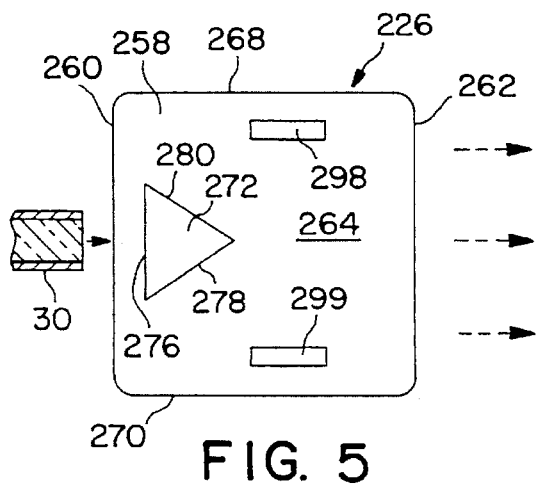
FIG. 5 is a schematic plan view of an alternate embodiment of the waveguide shown in FIG. 3, with the fiber optic distal end shown in cross-section.

For example, FIG. 5 depicts an illustrative waveguide 226 including a body portion 258 having a contained discontinuity 272 therein in the form of an equilateral triangle comprised of surfaces 276, 278 and 280 wherein the base surface 276 is positioned parallel with and adjacent incident face 260 of body portion 258.

Figure 6:
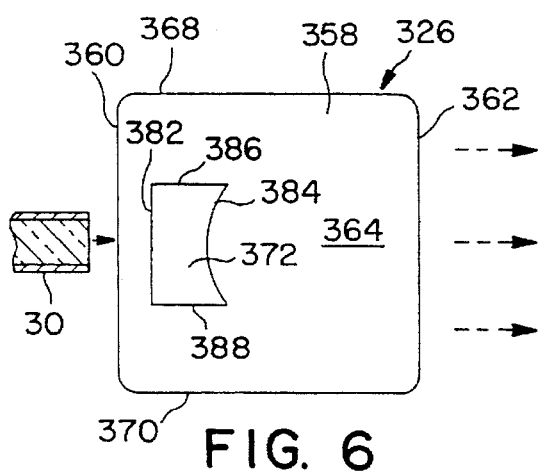
FIG. 6 is a schematic plan view of yet a further alternate embodiment of the waveguide shown in FIG. 3, with the fiber optic distal end shown in cross-section.

FIG. 6 depicts an illustrative waveguide 326 including a body portion 358 having a contained discontinuity 372 therein including a flat surface 382 parallel to and adjacent incident surface 360, a concave surface 384 opposite thereto, and two spaced apart side surfaces 386 and 388 extending between surfaces 382 and 384.

Figure 7:
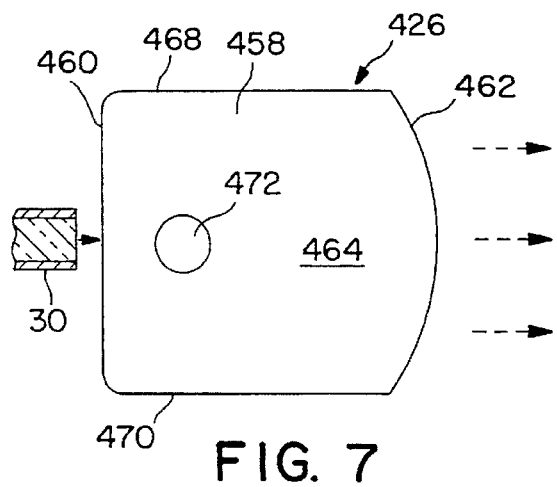
FIG. 7 is a schematic plan view of another alternate embodiment of the waveguide shown in FIG. 3, with the fiber optic distal end shown in cross-section.

In FIG. 7, contained discontinuity 472 is shown in combination with a convex emitting face 462.

Figure 8:
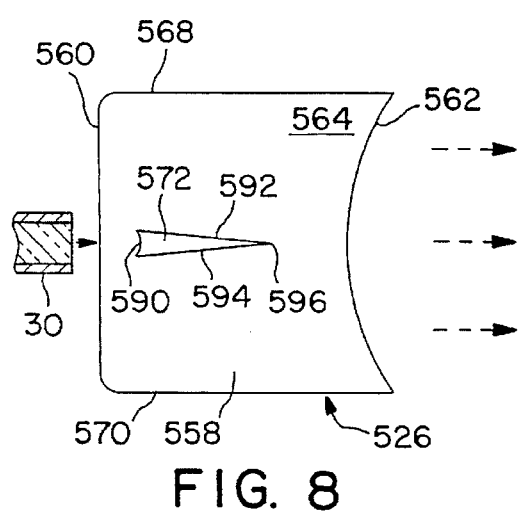
FIG. 8 is a schematic plan view of yet another alternate embodiment of the waveguide shown in FIG. 3, with the fiber optic distal end shown in cross-section.

FIG. 8 depicts an illustrative waveguide 526 including a body portion 558 having a contained discontinuity 572 including a convex surface 590 adjacent incident face 560 and two flat surfaces 592 and 594 extending from opposite ends of surface 590 toward concave emitting face 562 and terminating into a point 596.

Figure 10:
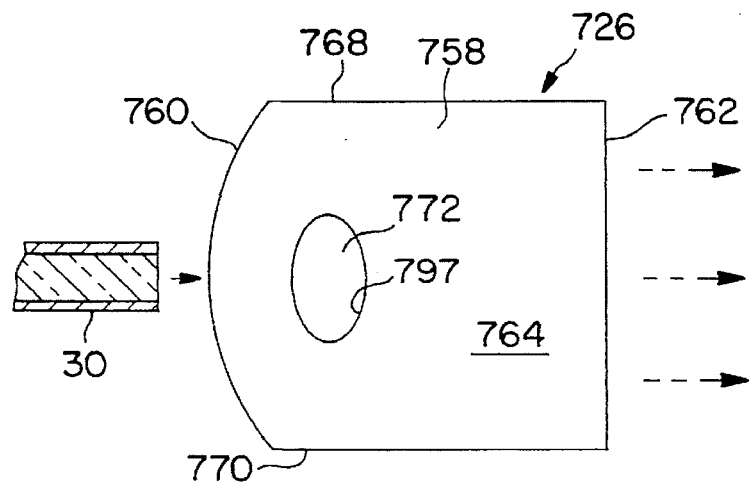
FIG. 10 is schematic plan view of still a further alternate embodiment of the waveguide shown in FIG. 3, with the fiber optic distal end shown in cross-section.

FIG. 10 depicts an illustrative waveguide 726 including a body portion 758 having a contained discontinuity 772 including an elliptical surface 797 together with a convex incident face 760.

In the illustrated embodiments described above, the discontinuities are positioned symmetrically about an axis substantially normal to the laser beam emitted from the fiber optic 30. However, asymmetric placement is also possible.

As shown in FIG. 5, body portion 258 of waveguide 226 may include therewithin more than one contained discontinuity such as additional diametrically opposed discontinuities 298 and 299 which are positioned on opposite or flanking sides of discontinuity 272 generally centrally between the incident and emitting faces 260 and 262 and adjacent side faces 268 and 270, respectively. Although discontinuities 298 and 299 are in the form of a rectangle, it is understood that they can take any other configuration deemed desirable for a particular application.

Each of the contained discontinuities depicted in FIGS. 3–11 can comprise any one or more of several beam expanding elements having indices of refraction less than the index of refraction of the respective body portions such as, but not limited to, a void in the body portions filled with air or a selected liquid. Where the discontinuity is a converter lens, i.e., a void, the surface(s) of the void are polished to assure good transmission. Alternatively, the surfaces can be sandblasted to diffuse the laser beam passing therethrough.

Figure 9:
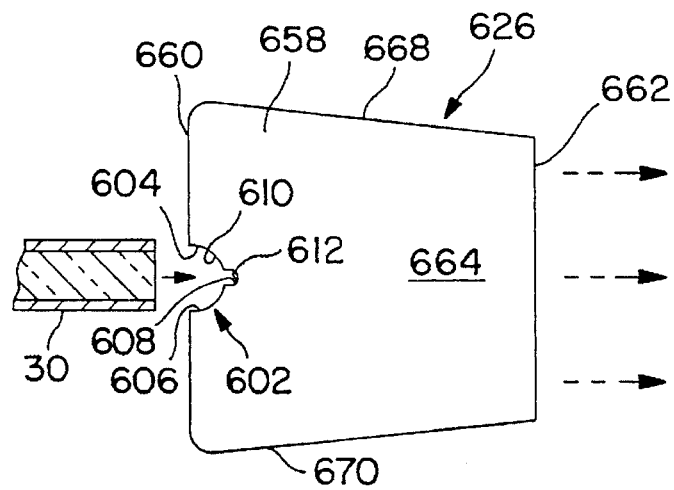
FIG. 9 is a schematic plan view of yet another alternate embodiment of the waveguide shown in FIG. 3, with the fiber optic distal end shown in cross-section.
Figure 11:
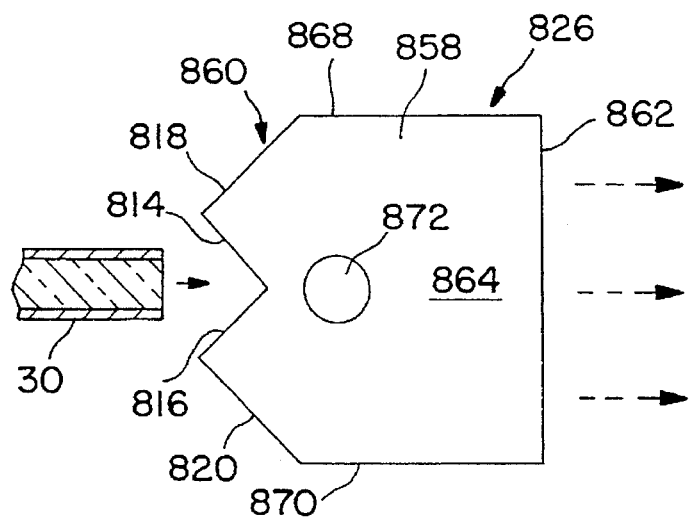
FIG. 11 is a schematic plan view of still yet another alternate embodiment of the waveguide shown in FIG. 3, with the fiber optic distal end shown in cross-section.

In addition to discontinuities within the body portion of the waveguide, the beam expander means of the present invention may also comprise one or more surface discontinuities in the incident face of the body portion of the waveguide as is shown in FIGS. 9 and 11.

FIG. 9 depicts an illustrative waveguide 626 including a body portion 658 with a particularly preferred surface discontinuity 602 in incident face 660 which is positioned centrally thereon and is defined by three contiguous arcuate surfaces 604, 606 and 608. Diametrically opposed arcuate surfaces 604 and 606 define a centrally positioned groove or cavity 610 which extends inwardly from incident face 660 into body portion 658. Surface 608, which is positioned between surfaces 604 and 606, defines a centrally positioned groove or cavity 612 which extends inwardly into body portion 658 from groove 610 and, more particularly, inwardly from arcuate surfaces 604 and 606. The groove 610 has a cross-sectional area greater than the cross-sectional area of the groove 612.

Waveguide 626 is in the form of a sphenoid, e.g., spatulate configuration, including a laser energy incident face 660, a laser energy emitting face 662, and peripheral faces 664–670 therebetween, i.e., top and bottom faces 664 and 666 (not shown) and side faces 668 and 670 which converge inwardly from the incident face 660 toward emitting face 662.

FIG. 11 depicts an illustrative waveguide 826 including a body portion 858 having a surface discontinuity in incident face 860 comprising a centrally positioned, wedge-shaped discontinuity including diametrically opposed flat surfaces 814 and 816 which converge inwardly toward emitting face 862. Incident face 860 further includes flat surfaces 818 and 820 which adjoin and diverge away from flat surfaces 814 and 816, respectively, toward peripheral faces 868 and 870 of body portion 858, respectively.

Waveguide 26 modifies the spatial as well as temporal characteristics of the laser beam emitted from the end of the distal fiber optic 30 into the waveguide 26 by refracting and reflecting the beam through one or more of the discontinuities described above. More particularly, the various discontinuities, either individually or in combination, receive the laser beam emitted from the distal end 34 of fiber optic 30, which has a substantially gaussian intensity profile, and transform and expand it into a relatively flat laser beam having a substantially square density profile which is emitted substantially uniformly along the length and width of the emitting face 62 to a degree such that the laser beam emitted from the waveguide 26 is at least three times wider than the beam thickness. As a result, the surgical instrument can be used to sweep a selected region of tissue in a manner similar to a paint brush.

Surgical instruments embodying the present invention are particularly well suited for heating the shoulder capsule to cross-link the collagen therein and shrinking and tightening the capsule to prevent inadvertent dislocations.

The invention can also be used to coagulate tonsils. While tonsillectomy is a very frequently performed surgical procedure, postoperative morbidity cannot always be avoided. The major problems noted with current tonsillectomy procedures are pain and bleeding, especially delayed bleeding. However, such problems can be substantially ameliorated by laser coagulation tonsillectomy, in particular when utilizing the present surgical instrument with a Nd:YAG (1.06 μm) laser at relatively low power levels in the range of about 5 to 10 watts. The Nd:YAG laser beam emitted by an instrument embodying the present invention can be used to irradiate the tonsils over a time period of about two to five minutes in a relatively slow and accurate painting-like motion over the tonsil surface to effect coagulation, i.e., until a slight blanching of the tonsil mucosa can be noticed.

Light energy at wavelengths from 400 to 1300 nanometers, such as from argon, KTP, Diode and Nd:YAG lasers, penetrates 1000 to 4000 microns into tissue and is desirable for deep coagulation. Light energy in pulsed form at wavelengths of 1800 to 2200 nanometers penetrates 200 to 500 microns into tissue and is suited for vaporization or heating and shrinkage of collagen in a shoulder capsule.

Additionally, and if desired, precautions against thermal damage to blood vessels, nerves and other structures lying beneath the tonsils can be taken by providing a saline pool as a heat sink, e.g., by preoperative injection of saline into the subcapsular space. Alternatively, a saline or water drip or spray can be sprayed onto the surface of the tissue such as the tonsil to cool the tissue and prevent or limit damage to the mucosa.

According to the present invention, the water or saline drip or spray is provided through the apertures 27 in stem 22. More particularly, water or saline solution is fed through the hub 41 and conduit 39, then through the conduit 33 via splice 37, then through the passageway defined by the interior passage 23 of stem 22, and finally through the passageway defined by apertures 27 in stem 22 and then onto the tissue surface to effect the cooling thereof.

Moreover, a cooling gas, such as nitrogen or carbon dioxide, can be applied to the tonsil surface to prevent damage to the epithelial layer or mucosa.

The components referred herein such as lasers, laser connectors, and optical fibers, all known in the art, have not described in detail herein and form no part of the present invention. Numerous variations and modifications of the embodiments described above may be effected without departing from the spirit and scope of the novel features of the invention. It is to be understood that no limitations with respect to the specific device illustrated herein are intended or should be inferred. It is, of course, intended to cover by the appended claims all such modifications as fall within the scope of the claims.

I claim:

1. A surgical instrument suitable for directing laser energy to a selected site comprising;
   (a) a hollow stem including a tip;
   (b) a fiber optic extending through said stem and including a proximal end adapted for coupling to a laser energy source and a distal end extending into said tip, said fiber optic being adapted to emit a beam of laser energy of a predetermined diameter through said distal end when coupled to said source;
   (c) a solid waveguide in said tip of said stem and positioned adjacent said distal end of said fiber optic, said waveguide including a transparent, splay body portion including a laser energy incident face and a laser energy emitting face as well as peripheral laser energy reflecting faces surrounding said body portion, said incident face being situated to receive a beam of laser energy emitted from said fiber optic; and
   (d) beam expander means unitary with said body portion for expanding the energy beam received through said incident face to produce an expanded energy beam emitted through said emitting face substantially uniformly along the length and width thereof, the expanded beam of laser energy having a thickness and a width which is at least three times the thickness of the expanded beam.

2. The surgical instrument of claim 1 wherein said splay body portion defines at least one discontinuity therein to provide said beam expander means, said discontinuity having an index of refraction different than the index of refraction of said body portion.

3. The surgical instrument of claim 2 wherein said discontinuity has an index of refraction less than the index of refraction of the body portion.

4. The surgical instrument of claim 2 wherein said discontinuity is centrally positioned in said body portion.

5. The surgical instrument of claim 2 wherein said body portion includes peripheral side faces, said body portion defining a first discontinuity positioned in said body portion generally centrally between said peripheral side faces and adjacent said incident face, and second and third discontinuities positioned on opposite sides of said first discontinuity generally centrally between said incident and emitting faces and adjacent said peripheral side faces.

6. The surgical instrument of claim 2 wherein said discontinuity is symmetrical about an axis substantially normal to the laser beam emitted from said fiber optic.

7. The surgical instrument of claim 2 wherein said discontinuity is a void defined by said body portion.

8. The surgical instrument of claim 2 wherein said discontinuity is a converter lens defined by said body portion.

9. The surgical instrument of claim 1 wherein said beam expander means is a discontinuity defined by said incident face.

10. The surgical instrument of claim 9 wherein said body portion includes peripheral side faces, said discontinuity having the configuration of a groove in said incident face positioned generally centrally thereon and extending into said body portion, said groove being situated to receive and expand said beam emitted from said fiber optic.

11. The surgical instrument of claim 9 wherein said body portion includes peripheral side faces coated with gold and said discontinuity comprises arcuate surfaces in said incident face that define a cavity in said body portion.

12. The surgical instrument of claim 1 wherein said beam expander means comprises a discontinuity defined by said incident face and at least one discontinuity defined within said body portion.

13. The surgical instrument of claim 1 wherein said stem includes an outer surface and an inner surface defining a hollow interior passageway for said fiber optic and a fluid for cooling said selected site, said stem including an aperture located adjacent the tip thereof, said aperture extending between said inner and outer surfaces of said stem and defining a passageway for the cooling fluid.

14. The surgical instrument of claim 13 wherein said stem includes a distal end and a proximal end, the cooling fluid being fed into said proximal end of said stem via a conduit connected to the distal end of said stem.

15. The surgical instrument of claim 13 wherein said stem includes a distal end and a proximal end, said fiber optic extending through a first conduit connected to the proximal end of said stem, said instrument further including a second conduit connected to the first conduit, said first and second conduits defining a passageway for said cooling fluid.

16. The surgical instrument of claim 15 further including a splice for splicing said first and second conduits together.

17. A surgical instrument suitable for directing laser energy to a selected site for performing a medical procedure comprising;

(a) a hollow housing including a tip;

(b) a fiber optic extending through said housing and terminating in a distal end that extends into said tip, said fiber optic distal end being adapted to emit a beam of laser energy;

(c) a transparent, plate-like waveguide in said tip adjacent said distal end of said fiber optic, said waveguide including a laser energy incident face, a laser energy emitting face, and peripheral laser energy reflecting surfaces; and defining at least one discontinuity providing a region having an index of refraction less than the index of refraction of the waveguide for expanding the beam of laser energy received through said incident face to produce an expanded beam of laser energy emitted through said emitting face substantially uniformly along the length and width thereof, the expanded beam of light energy having a thickness and a width which is at least three times the thickness thereof.

18. The surgical instrument of claim 17 wherein said peripheral laser energy surfaces are provided with a gold coating.

19. The surgical instrument of claim 17 wherein said peripheral surfaces include side faces and a first discontinuity is defined by said waveguide generally centrally between said peripheral side faces and adjacent said incident face, and second and third discontinuities are defined by said waveguide flanking said first discontinuity.

20. The surgical instrument of claim 17 wherein said discontinuity is a void defined in the waveguide.

21. The surgical instrument of claim 17 wherein said discontinuity is a converter lens defined by said waveguide.

22. The surgical instrument of claim 17 wherein said housing includes an outer surface and an inner surface defining an interior hollow passageway for said fiber optic and a fluid for cooling said selected site, said housing including an aperture adjacent said tip thereof, said aperture extending between said inner and outer surfaces of said housing and defining a passageway for the cooling fluid.

23. A surgical instrument suitable for directing laser energy to a selected site comprising:

(a) a hollow housing including a tip;

(b) a fiber optic extending through said housing and including a proximal end adapted for coupling to a laser energy source and a distal end extending into said tip, said fiber optic being adapted to emit a beam of light energy of a predetermined diameter through said distal end when coupled to said source;

(c) a solid, transparent, plate-like waveguide in said tip adjacent the distal end of said fiber optic, said waveguide including a laser energy incident face, a laser energy emitting face, and peripheral laser energy reflecting surfaces, said incident face receiving the beam of laser energy emitted from said fiber optic; and (d) said incident face defining at least one surface discontinuity for receiving and expanding the beam of laser energy received through said incident face to produce an expanded beam of laser energy emitted through said emitting face substantially uniformly along the length and width thereof, the expanded beam of laser energy having a thickness and a width which is at least three times the thickness of said expanded beam.

24. The surgical instrument of claim 23 wherein said surface discontinuity is wedge-shaped.

25. The surgical instrument of claim 23 wherein said surface discontinuity includes first and second opposed flat surfaces that converge toward the emitting face.

26. The surgical instrument of claim 23 wherein said surface discontinuity is defined by at least three contiguous arcuate surfaces.

27. The surgical instrument of claim 23 wherein said housing includes an outer surface and an inner surface defining an interior hollow passageway for said fiber optic and a fluid for cooling said selected site, said housing including an aperture adjacent said tip thereof, said aperture extending between said inner and outer surfaces of said housing and defining a passageway for the cooling fluid.

28. A surgical instrument suitable for directing light energy to a selected site comprising:

(a) a hollow elongate housing;

(b) a generally flat tip member at the end of said housing including a base and spaced apart arms extending outwardly from said base;

(c) a fiber optic extending through said housing including a proximal end adapted for coupling to a light energy source and a distal end extending into said tip member, said fiber optic being adapted for emitting a beam of light energy through said distal end; and (d) a solid laser energy waveguide in said tip member between said spaced apart arms, said waveguide including a transparent body portion having a laser energy incident face at one end thereof, a laser energy emitting face at the other end thereof, and peripheral side faces therebetween abutting said arms of said tip member substantially along the entire length of said waveguide.

29. The surgical instrument of claim 28 wherein said tip member further includes top and bottom support plates secured thereto and said body portion is mounted therebetween.

30. The surgical instrument of claim 29 wherein one of said plates is removably secured to said arms.

31. The surgical instrument of claim 30 wherein a shoulder extends around the periphery of said base portion and said arms of said tip member, the peripheral edge of said removably secured plate being seated in and abutting said shoulder.

32. The surgical instrument of claim 28 wherein said emitting face is substantially flush with said arms.

33. The surgical instrument of claim 28 wherein said emitting face extends beyond said arms.

34. The surgical instrument of claim 28 wherein said body portion has a spatulate configuration.

35. The surgical instrument of claim 28 wherein said body portion has a quadrate configuration.

36. The surgical instrument of claim 28 wherein said body portion has a sphenoid configuration.

37. The surgical instrument of claim 28 wherein the body portion defines therewithin a discontinuity having an index of refraction which is less than the index of refraction of said body portion.

38. The surgical instrument of claim 28 wherein a distal end portion of the fiber optic is secured in the tip member with an elastomeric potting compound.

39. The surgical instrument of claim 38 wherein the potting compound is a silicone resin.

40. The surgical instrument of claim 38 wherein the potting compound is a room temperature vulcanizable silicone resin.

41. The surgical instrument of claim 28 wherein said housing includes an outer surface and an inner surface defining an interior hollow passageway for said fiber optic and a fluid for cooling said selected site, said housing including an aperture adjacent the tip thereof, said aperture extending between said inner and outer surfaces of said housing and defining a passageway for the cooling fluid.

* * * * *